United States Patent [19]

Takaku et al.

[11] 4,361,572
[45] Nov. 30, 1982

[54] TETRAHYDRONICOTINAMIDE DERIVATIVE, PHARMACEUTICAL COMPOSITIONS AND USE

[75] Inventors: Sakae Takaku, Ageo; Fumiaki Matsuura, Tokyo; Takashi Mori, Ohizumigakuenmachi; Yasushi Murakami, Tokyo; Shigeyuki Kataoka, Sakado; Yasuhisa Takeda, Ichikawa; Yasuhiro Yamashita, Togoshi; Yumiko Takeda, Ichikawa; Takashi Matsuno, Ohmiya; Koji Mizuno, Kawagoe; Shinichi Kaiho, Chiba; Tamotsu Yamazaki, Tokorozawa; Shun-ichi Hata, Yokohama; Shigeru Takanashi, Asaka, all of Japan

[73] Assignee: Chugai Seiyaku Kabushiki Kaisha, Tokyo, Japan

[21] Appl. No.: 332,856

[22] Filed: Dec. 21, 1981

[51] Int. Cl.³ .................. A61K 31/455; C07D 211/78
[52] U.S. Cl. .................................... 424/266; 546/261; 546/262; 546/316
[58] Field of Search .............. 546/261, 262, 316; 424/266

[56] References Cited

U.S. PATENT DOCUMENTS 3,462,532  8/1969  Hardy ................................. 546/316
3,505,342  4/1970  Wender et al. .................... 546/316

OTHER PUBLICATIONS

Acta Chemica Scandinavica 11 (1957), pp. 1183–1190, "Local Anaesthetics I, N-Alkyl Pyrrolidine and N-Alkyl Piperidine Carboxylic Acid Amides"-Ekenstam et al.

Primary Examiner—Robert W. Ramsuer
Attorney, Agent, or Firm—Browdy and Neimark

[57] ABSTRACT

1,4,5,6-Tetrahydronicotinamide derivative represented by the formula:

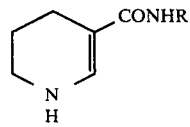

(wherein R is defined in the specification), a process of preparing the same and pharmaceutical composition containing the same are disclosed.

The compound has action for suppressing aggregation of platelets, and antiinflammatory, antipyretic and analgesic actions.

23 Claims, No Drawings

TETRAHYDRONICOTINAMIDE DERIVATIVE, PHARMACEUTICAL COMPOSITIONS AND USE

This invention relates to a 1,4,5,6-tetrahydronicotinamide derivative of the formula:

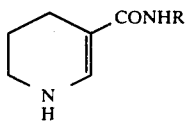

(wherein R is a phenyl or pyridyl group which may have one or more substituents), a process for producing the same and a pharmaceutical composition comprising the same.

In the formula (I), the substituent of the phenyl and pyridyl is, for example, an alkyl group containing 1-4 carbon atoms, an alkoxy group containing 1-4 carbon atoms or a halogen atom.

The compound of this invention is produced by partially reducing, for example, a nicotinamide derivative of the formula:

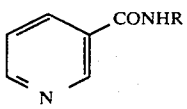

(wherein R has the same meaning as defined above). The reduction is performed by introducing hydrogen gas in the presence of a catalyst in a solvent such as tetrahydrofuran, dioxane, alcohol, hydrous alcohol or acetic acid, preferably alcoholic solvents. Commonly employed metal catalysts are used, and palladium-on-carbon is particularly preferred. A Raney-nickel catalyst may also be used. The reaction temperature is in the range of from 0° to 100° C., preferably from 10° to 50° C., and the reaction is completed by having the nicotinamide derivative absorb about 2 mols of hydrogen at a hydrogen pressure of 1 to 50 atm., preferably 2 to 5 atm.

The so obtained compound of this invention is useful as a medicine since it has not only high ability to suppress aggregation of platelets but also antiinflammatory, antipyretic and analgesic effects.

Experiments with animals have shown that many antiinflammatory agents have ability to suppress aggregation of platelets. But it has been pointed out that one defect of these antiinflammatory agents is that when administered to living organisms, they suppress the prostaglandin $I_2$ activity in the walls of the arteries and with extended administration, they accelerate the aggregation of platelets on the arterial walls. The compound of this invention is free from these defects and is used as an effective agent to prevent and cure thrombosis and is also effective as antiinflammatory and antipyrectic analgesic agents.

When used as a medicine, the compound of this invention is formulated by a conventional technique into a tablet, granule, powder, capsule or injection, and administered to patients either orally or parenterally. A tablet, granule, powder or capsule is prepared by mixing the compound with a pharmaceutical carrier such as lactose, starch, dextrin, sucrose, crystalline cellulose, kaolin, calcium carbonate, talc or magnesium stearate. An injection is prepared by dissolving the compound in distilled water or a solution of salt such as sodium chloride or potassium chloride.

The dosage of the compound of this invention is 5–300 mg/Kg/day, preferably 10–150 mg/Kg/day, for oral administration, and is 0.5–100 mg/Kg/day, preferably 1–50 mg/Kg/day, for parenteral administration. The desired amount is administered in a single dose or in several doses daily.

This invention is now described in greater detail by reference to the following experiment and examples to which this invention is by no means limited.

Experiment: Effect of preventing acute pulmonary thromboembolic death of mice

Six-week-old male ddY/SPF strain mice were administered orally with 200 mg/Kg of the compounds of Examples 9 and 10 and the active controls. Four hours later, the mice were intravenously administered with 325 mg/Kg of ADP and 140 mg/Kg of sodium arachidonate. The number of the mice that were dead within 24 hours of the administration of ADP and sodium arachidonate was counted and the results are shown in the table below. As a reference compound, ticlopidine and sulfinpirazone were used and their efficacy to prevent acute thrombosis was compared with that of the compounds of this invention.

TABLE
Effect of Compounds of the invention against Acute Pulmonary Thromboembolic Death

| Test Compound | ADP | | Arachidonic Acid | |
|---|---|---|---|---|
| | No. of Dead Mice | Inhibition % | No. of Dead Mice | Inhibition % |
| Ticlopidine | 9/20 | 40 | 7/20 | 36 |
| Sulfinpirazone | 16/20 | −7 | 8/20 | 27 |
| Compound of Ex. 9 | 9/20 | 40 | 4/20 | 64 |
| Compound of Ex. 10 | 6/20 | 60 | 7/20 | 36 |
| Control | 30/40 | — | 11/20 | — |

EXAMPLE 1

Twenty-seven grams of N-nicotinoyl-2-methoxyaniline was dissolved in 800 ml of 10% hydrous ethanol. To the solution, 5 g of 10% palladium-on-carbon was added and the mixture was hydrogenated at 40° to 50° C. under atmospheric pressure. After 2 mols of hydrogen was introduced over a period of about 6 hours, the reaction was stopped and the catalyst was removed. The liquid reaction mixture was concentrated and the residual oil was purified with column chromatography on silica gel and recrystallized from hydrous methanol to give N-(1,4,5,6-tetrahydronicotinoyl)-2-methoxyaniline having a melting point of 126°–128° C. Yield=60%

Elemental analysis: Calculated for $C_{13}H_{16}N_2O_2$: C 67.2; H 6.9; N 12.1 (%); Found: C 67.2; H 6.8; N 12.0 (%).

EXAMPLE 2

By reducing and purifying N-nicotinoyl-3-methoxyaniline as in Example 1, N-(1,4,5,6-tetrahydronicotinoyl)-3-methoxyaniline having a melting point of 173° to 176° C. was produced. Yield=58%.

Elmental analysis: Calculated for $C_{13}H_{16}N_2O_2$: C 67.2; H 6.9; N 12.1 (%); Found: C 67.3; H 7.0; N 12.2 (%).

EXAMPLE 3

As in Example 1, N-nicotinoyl-4-methoxyaniline was treated and recrystallized from ethyl acetate/ether to give N-(1,4,5,6-tetrahydronicotinoyl)-4-methoxyaniline having a melting point of 112° to 115° C. Yield=64%.

Elemental analysis: Calculated for $C_{13}H_{16}N_2O_2$: C 67.2; H 6.9; N 12.1 (%); Found: C 67.1; H 6.7; N 12.0 (%).

EXAMPLE 4

As in Example 1, N-nicotinoyl-2,6-dimethylaniline was reduced at 45° C. and the crystal formed by concentration was recrystallized from hydrous methanol to give N-(1,4,5,6-tetrahydronicotinoyl)-2,6-dimethylaniline having a melting point of 119° to 122° C. Yield=62%.

Elemental analysis: Calculated for $C_{14}H_{18}N_2O$: C 73.0; H 7.9; N 12.2 (%); Found: C 72.9; H 7.8; N 12.1 (%).

EXAMPLE 5

As in Example 1, N-nictinoyl-2-methylaniline was reduced and purified, and recrystallized from methanol/ether to give N-(1,4,5,6-tetrahydronicotinoyl)-2-methylaniline having a melting point of 141° to 144° C. Yield=61%.

Elemental analysis: Calculated for $C_{13}H_{16}N_2O$: C 72.2; H 7.5; N 13.0 (%); Found: C 72.1; H 7.6; N 13.1 (%).

EXAMPLE 6

Fifty grams of N-nicotinoyl-2-fluoroaniline was dissolved in 700 ml of 10% hydrous ethanol. To the solution, 5 g of 10% palladium-on-carbon was added and the mixture was reduced with hydrogen at room temperature and at atmospheric pressure. When a stoichiometric amount of hydrogen was absorbed, the reaction was stopped and the catalyst was removed. the liquid reaction mixture was concentrated and the resulting crystal was recrystallized from hydrous methanol to give N-(1,4,5,6-tetrahydronicotinoyl)-2-fluoroaniline having a melting point of 137° to 140° C. Yield=70%.

Elemental analysis: Calculated for $C_{12}H_{13}N_2OF$: C 65.4; H 5.9; N 12.7 (%); Found: C 65.2; H 5.7; N 12.5 (%).

EXAMPLE 7

By reducing N-nicotinoylaniline as in Example 6 except that the hydrogen pressure was 4 atm., N-(1,4,5,6-tetrahydronicotinoyl)aniline having a melting point of 209° to 212° C. was produced. Yield=63%.

Elemental analysis: Calculated for $C_{12}H_{14}N_2O$: C 71.3; H 7.0; N 14.0 (%); Found: C 71.4; H 7.1; N 13.8 (%).

EXAMPLE 8

As in Example 6, 2-nicotinamidopyridine was reduced and recrystallized from tetrahydrofuran ether to give 2-(1,4,5,6-tetrahydronicotinamido)pyridine having a melting point of 156° to 159° C. Yield=68%.

Elemental analysis: Calculated for $C_{11}H_{13}N_3O$: C 65.0; H 6.5; N 20.7 (%); Found: C 64.9; H 6.4; N 20.6 (%).

EXAMPLE 9

As in Example 1, N-nicotinoyl-2,5-dimethoxyaniline was hydrogenated. After removing the catalyst, the solvent was concentrated and the resulting oil was purified by column chromatography on silica gel and recrystallized from methanol/ether to give N-(1,4,5,6-tetrahydronicotinoyl)-2,5-dimethoxyaniline having a melting point of 124° to 126° C. Yield=60%.

Elemental analysis: Calculated for $C_{14}H_{18}N_2O_3$: C 64.1; H 6.9; N 10.7 (%); Found: C 64.0; H 6.8; N 10.8 (%).

EXAMPLE 10

As in Example 1, N-nicotinoyl-2-ethoxyaniline was hydrogenated. After removal of the catalyst, the solvent was concentrated and the resulting crystal was recrystallized from methanol/water to give N-(1,4,5,6-tetrahydronicotinoyl)-2-ethoxyaniline having a melting point of 145° to 146° C. Yield=62%.

Elemental analysis: Calculated for $C_{14}H_{18}N_2O_2$: C 68.3; H 7.4, N 11.4 (%); Found: C 68.2; H 7.5; N 11.3 (%).

What is claimed is:

1. A 1,4,5,6-tetrahydronicotinamide derivative of the formula:

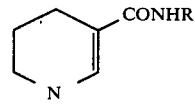

(wherein R is a phenyl or pyridyl group which may have one or more alkyl groups containing 1-4 carbon atoms, alkoxy groups containing 1-4 carbon atoms or halogen atoms as substituents) or a salt thereof.

2. N-(1,4,5,6-Tetrahydronicotinoyl)-2-methoxyaniline.
3. N-(1,4,5,6-Tetrahydronicotinoyl)-3-methoxyaniline.
4. N-(1,4,5,6-Tetrahydronicotinoyl)-4-methoxyaniline.
5. N-(1,4,5,6-Tetrahydronicotinoyl)-2,5-dimethoxyaniline.
6. N-(1,4,5,6-Tetrahydronicotinoyl)-2-ethoxyaniline.
7. N-(1,4,5,6-Tetrahydronicotinoyl)-2-methylaniline.
8. N-(1,4,5,6-Tetrahydronicotinoyl)-2,6-dimethylaniline.
9. N-(1,4,5,6-Tetrahydronicotinoyl)-2-fluoroaniline.
10. N-(1,4,5,6-Tetrahydronicotinoyl)aniline.
11. 2-(1,4,5,6-Tetrahydronicotinamido)pyridine.
12. A pharmaceutical composition comprising a 1,4,5,6-tetrahydronicotinamide derivative in accordance with claim 1 and a pharmaceutically acceptable carrier.
13. A pharmaceutical composition according to claim 12 which is formulated in the form of a tablet, granule, powder or capsule for oral administration.
14. A pharmaceutical composition according to claim 13 which uses lactose, starch, dextrin, sucrose, crystalline cellulose, kaolin, calcium carbonate, talc or magnesium stearate as a carrier.
15. A pharmaceutical composition according to claim 12 which enables the administration of the tetrahydronicotinamide derivative in an effective dose of 5-300 mg/Kg per day.
16. A pharmaceutical composition according to claim 15 which enables the administration of the tetrahydronicotinamide derivative in an effective dose of 10-150 mg/Kg per day.
17. A pharmaceutical composition according to claim 12 which is formulated in the form of an injection.

18. A pharmaceutical composition according to claim 17 which uses distilled water or an aqueous solution of sodium chloride or potassium chloride as a carrier.

19. A pharmaceutical composition according to claim 17 which enables the administration of the tetrahydronicotinamide derivative in an effective dose of 0.5-100 mg/Kg per day.

20. A pharmaceutical composition according to claim 17 which enables the administration of the tetrahydronicotinamide derivative in an effective dose of 1-50 mg/Kg per day.

21. A method for the prevention or treatment of thrombosis comprising orally or parenterally administering to a patient in need of such treatment an effective amount of a compound in accordance with claim 1.

22. A method for providing an antiinflammatory effect comprising orally or parenterally administering to a patient in need of such treatment an effective amount of a compound in accordance with claim 1.

23. A method for providing antipyretic analgesic effects comprising orally or parenterally administering to a patient in need of such treatment an effective amount of a compound in accordance with claim 1.

* * * * *